United States Patent [19]
Liss et al.

[11] Patent Number: 5,571,149
[45] Date of Patent: *Nov. 5, 1996

[54] NON-INTRUSIVE ANALGESIC NEUROAUGMENTIVE AND IONTOPHORETIC DELIVERY APPARATUS AND MANAGEMENT SYSTEM

[75] Inventors: Saul Liss, Hawthorne; Bernard Liss, Glen Rock, both of N.J.

[73] Assignee: E.P., Inc., Paterson, N.J.

[ * ] Notice: The term of this patent shall not extend beyond the expiration date of Pat. No. 5,109,847.

[21] Appl. No.: 227,014

[22] Filed: Apr. 13, 1994

Related U.S. Application Data

[63] Continuation-in-part of Ser. No. 82,131, Jun. 23, 1993, abandoned, and a continuation-in-part of Ser. No. 127,163, Sep. 27, 1993, Pat. No. 5,421,817, which is a continuation-in-part of Ser. No. 877,873, May 4, 1992, abandoned, which is a continuation of Ser. No. 703,610, May 21, 1991, Pat. No. 5,109,847.

[51] Int. Cl.⁶ .................................................. A61N 1/18
[52] U.S. Cl. ................... 607/72; 604/20; 607/46
[58] Field of Search ........................ 604/20; 607/46, 607/72

[56] References Cited

U.S. PATENT DOCUMENTS 5,109,847   5/1992   Liss et al. .................................. 607/72
5,135,478   8/1992   Sibalis ....................................... 604/20

*Primary Examiner*—William E. Kamm
*Assistant Examiner*—Scott M. Getzow
*Attorney, Agent, or Firm*—Hopgood, Calimafde, Kalil & Judlowe

[57] ABSTRACT

The present invention pertains to a portable non-invasive electronic apparatus which can be used to relieve pain or alter the symptoms of certain neurological dysfunctions. A specifically contoured constant current and current limited waveform is generated and applied to selectively positioned electrodes. A program controlled processor tracks usage of the unit to prevent abuse and monitor progress. An overall treatment regimen centered on the stimulator may be effected simply and safely. The invention also provides an apparatus and method for the iontophoretic topical administration of a pharmaceutical agent. The apparatus is operated in a monopolar mode with a particular complex waveform which synergistically enhances the amount of various neurobiochemical species in the cerebral spinal fluid and the blood plasma.

20 Claims, 4 Drawing Sheets

CARRIER FREQUENCY
15,000 hz MONOPOLAR

1st MODULATOR
15 hz

2nd MODULATOR
500 hz

TYPICAL COMBINED
WAVEFORM (MONOPOLAR)

TYPICAL COMBINED
WAVEFORM (BIPOLAR)

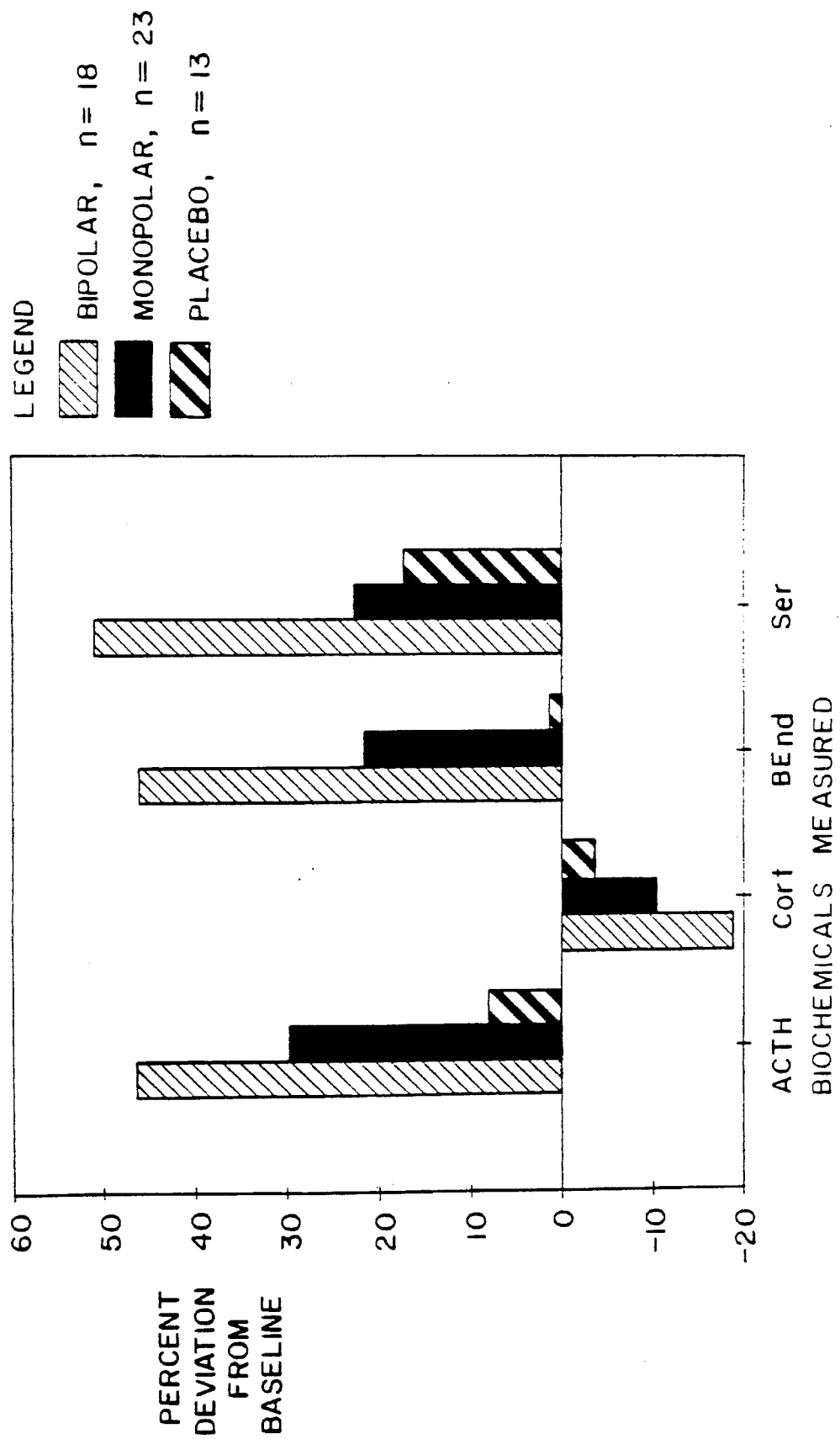

NON-INTRUSIVE ANALGESIC NEUROAUGMENTIVE AND IONTOPHORETIC DELIVERY APPARATUS AND MANAGEMENT SYSTEM

This application is a continuation-in-part of application Ser. No. 82,131, field Jun. 23, 1993, now abandoned, and of application Ser. No. 127,163, now U.S. Pat. No. 5,421,817, filed Sep. 27, 1993, each of which is a continuation-in-part of application Ser. No. 877,873, filed May 4, 1992, now abandoned, which is a continuation of application Ser. No. 703,610, filed May 21, 1991, now U.S. Pat. No. 5,109,847, the disclosures of which are all incorporated herein by reference.

BACKGROUND OF THE INVENTION

1. The Field of the Invention

The invention of our prior application, now U.S. Pat. No. 5,109,847, generally relates to an apparatus that modulates the neurological responses associated with certain biological dysfunctions, neural pain, and pain caused by blood flow deficiency. More specifically, it is an apparatus and system for the treatment of selected pain and/or neural dysfunction-induced maladies.

The present relates to improvements thereof; more specifically, an apparatus for the topical iontophoretic administration of medication for the treatment of various conditions, and an apparatus for modulating neural responses using an additional modulation frequency.

2. The State of the Art

The sensation of pain is associated with numerous physiological and psychological ailments and is a universal experience of all complex living organisms. Pain, as the mental manifestation of a neurological response, is an important biological attribute and is critical to living and enabling a person to understand dangers in the environment and to adapt thereto. Concomitant with this important role, the alleviation of pain has been a fundamental goal of medicine and philosophy for as long as the medical profession has existed. Indeed, the ability to control the neurological pathways through which pain is conveyed has made complex procedures far simpler to implement and much less traumatic to the patient.

There is a class of neurological response which is associated with pain that does not correspond to or act as a warning for a particular physical damage or biological dysfunction. In fact, many biologically important transitions are characterized by significant pain, such as the withdrawal period of an addict, during which time the addict's system is depleted of a specific endogenous narcotic. Other mental conditions which are neurologically response-dependent conditions include depression, hypertension, causalgia pain, insomnia and jet lag. Analogous to pain being an indication that the local environment is being dangerous, occurrences such as jet lag and drug withdrawal are both essentially a severe change in a person's environment.

The importance of the ability to control neurological response and associated perceptions of pain and distress has led to the development of many pain control methodologies. The most common of which employs bio-active chemical agents that act to block neural transmission pathways within the body. These are designed to operate locally for spot treatment or broadly for generalized control or inhibition of pain response throughout the body. Chemical interference with pain signals has broad based appeal, but in many instances is unacceptable. For example, some chemicals have toxic side affects or cause allergic reactions to certain patients. For more chronic ailments, such as chronic migraine headache syndrome, repeated absorption of chemical narcotics may reduce the associated pain, but at unacceptably high costs associated with interference with routine activities, addiction, and/or toxicity of the narcotic.

In view of the problems associated with chemical pain control, efforts have abounded to discover treatment approaches which would not involve pharmacological (chemical) interference with neural transmitters in the body. One approach that has recently sparked tremendous interest is the use of low power electrical stimulator devices capable of passing currents across key neural transmitter junctions in the body and thus effecting a blockage of neurological pathways which are inducing messages of pain to the brain. A practical implementation of this approach is disclosed in U.S. Pat. No. 3,902,502 to Liss, et al; the teachings of which are herein incorporated by reference.

The system disclosed in the '502 patent presented a pulsed direct current waveform having a high frequency carrier modulated by a single low frequency modulation. It was discovered that this waveform was particularly successful at controlling symptoms of certain neurological disorders.

Although effective for its applied treatment, many electrical stimulatory devices are limited to certain applications and lack the requisite flexibility for broad-based appeal. In addition, a drawback to the use of electrical stimulation to control pain is the concern by patients and others about the impact of power dissipation on the patient. Although low current, the power dissipation of many of the electrical stimulation devices is still quite significant. Efforts to reduce the applied power have resulted in stimulation devices with little or no physiological impact.

There has been, therefore, a search for new electrical stimulation devices characterized by exceptional pain management capabilities while reducing the overall patient exposure to electrical energy.

It is also clear that pain can be caused by organic physiologic conditions, trauma, infections, and the like. While systemic analgesic agents have been used with some success, it is often desirable to attempt administration directly to the area of the patient where the medication is required. This concept also has application to the administration of a wide variety of pharmacological agents. For example, Joseph Kleinkort delivered a presentation almost a decade ago at the USAFE Medical Convention in Garmisch, Germany, in which he described to iontophoretic administration of hydrocortisone; the technique was referred to as transionic injection. Using two moistened electrodes and a particular type of micronized hydrocortisone dispersed in a petrolatum ointment base, it was found that transionic injection was as effective as percutaneous injection. The apparatus used by Kleinkort provided an electrical waveform to the electrodes which consisted of a carrier frequency of 12–20 KHz and a modulation frequency of 8–20 Hz.

More recently, Sibalis in U.S. Pat. No. 5,135,478, the disclosure of which is incorporated herein by reference, described an electrical transdermal drug applicator which provides a particular waveform to counteract the apparent decrease in the amount of the pharmaceutical delivered as the duty cycle of the apparatus increases (i.e., the time during which current is "on" relative to the time current is "off"). Sibalis provides a waveform to the electrodes which comprises a negative conditioning pulse and a sequence of different waveforms which dilate blood vessels, impede coagulation and vasoconstriction, and thereby allow for better transdermal delivery of the drug. The complex waveform generally uses an AC carrier frequency of 1.5–3.5 MHz, a pulse width of 1.25–11.25 ms, and is modulated by both an AC modulated :square wave at 250 Hz and a second AC modulator at 570–870 Hz.

There is yet a need for the improved transdermal delivery of drugs, including improved tissue wetting management, minimization of the amount of electrical energy delivered to the patient, improved patient response and comfort with the procedure, and there is especially a need to tailor the aspects of delivery with respect to the particular drug or combinations of drugs used.

SUMMARY AND OBJECTS OF THE PRESENT INVENTION

This invention may be summarized, at least in part with reference to its objects.

It is, therefore, an object of the present invention to provide an apparatus for the selective generation of low current nerve stimulation waveforms configured to control pain and/or reduce the symptoms of certain neurological dysfunctions..

It is another object of the present invention to provide an apparatus for generating a complex waveform that when applied to a patient involves very low power dissipation.

It is a further object of the present invention to provide a pain control system that includes a means for creating a complex waveform and a data processing means for managing and recording the implementation of that waveform.

It is yet another object of the present invention to provide a method for low power, electrically induced analgesic treatment by the placement of at least two electrodes on selected neurologically important sites and the controlled introduction of a complex waveform for a predetermined time forming a treatment regimen.

It is still another object of the present invention to provide a method for treating the neurological dysfunctions associated with such ailments as migraine headaches, dental procedures, PMS and drug withdrawal.

The above and other objects of the present invention are realized in a specific illustrative electrical stimulator device. This device includes a small DC power source and a means for converting the current output of the power source into a complex waveform as an output across two or more electrodes attached to the patient's body. The complex waveform includes a carrier frequency with at least two low frequency modulations. The carrier frequency will range between 1 KHz and 300 GHz. The first modulation to this carrier wave will have a frequency between 0.01 and 199 kilohertz (i.e., between 10 Hz and 199 KHz). The second modulation to the carrier will have a frequency range between 0.1 and 300 kilohertz (i.e., between 100 Hz and 300 KHz). An optional third modulation to the carrier will have a frequency in the range between about 0.1 and 1,000 Hz. Each modulation to the carrier is preferably a pulse train in the form of a square waveform.

The placement of the electrodes will depend on the ailment of the subject of treatment, and the frequency of treatment will depend on the severity of the pain or dysfunction.

In accordance with the varying aspects of the present invention, the stimulator device may include a digital delta processor and stored programming for enhanced implementation of the prescribed treatment. In this manner, the program controlling the output of the stimulator will prevent use beyond a number of times and beyond the time set for each use. The limits of number of uses and of length of time for each use will be set by the prescribing physician. This promotes and enhances the use of expressly developed treatment regimens by a prescribing physician. The patient's progress can be compared to patient compliance in the context of continuing the prescription or altering same on behalf of the patient.

In our improved invention, one object is to provide an improved tissue-electrode interfacial environment to provide the transdermal delivery of the pharmaceutical agent.

Another object of our invention is to minimize the amount of electrical energy which must be applied to the patient to enable a suitable dosage of the drug to be administered.

Yet another object of the invention is to avoid harsh sensation response to the electrical energy, thereby improving patient comfort and compliance with the procedure.

Still another object of the invention is to tailor the characteristics of the electrical energy to the particular drug being administered to the patient to enhance the administration and/or the efficacy of the drug delivered.

In particular, the present invention also provides an improved apparatus which comprises the aforementioned electrical stimulator device having two moist electrodes, at least one of which is contains a pharmaceutical agent in a suitable carrier. The complex waveform used during iontophoretic transdermal administration includes a carrier signal operating at 1–300 KHz, a first modulating frequency operating at 0.01–199 KHz (10–99,000 Hz), and a second modulation frequency operating at 0.1–300 KHz (100–300, 000 Hz). The waveform is preferably monopolar, or at least is essentially monopolar in order to provide a net electrophoretic driving force for diffusion of the pharmaceutical agent into the patient.

The foregoing features of the present invention may be more fully understood in view of the illustrative description presented below and the claims.

BRIEF DESCRIPTION OF THE FIGURES

FIG. 4 is a chart of the effect of the inventive apparatus on certain neurotransmitters.

DESCRIPTION OF PREFERRED EMBODIMENTS

Figure 1A:
FIGS. 1A–1E are representations of sample carrier, modulation, and composite waveforms utilized in the present invention.

Discussing the present invention first in overview, it is a fundamental diserratum to provide a portable non-invasive analgesia inducing apparatus that exhibits a selectively developed complex waveform of electrical output. This output is applied between at least two contact probes for generating intracorporal current. The placement of the probes will depend on the treatment regimen. For example, migraine headache syndrome may involve the placement of the contacting probes on each side of the patient's cranium, one at the primary site of pain and the second at the contralateral trapezius insertion. Other locations may include intraoral, e.g., for local analgesia to control the pain associated with a dental restoration procedure.

Although the theory describing the underlying pain control phenomenon is not well known or, for that matter, even established, and while not desirous of being constrained to a particular theory, it is generally believed that the introduction of an intracorporal current acts upon the electrically conducted neural transmitters of the patient. It has been discovered that the particular complex waveform of the present invention when applied to a patient creates distinct changes in the blood plasma and cerebral spinal fluid concentration of such compounds as melatonin, serotonin, beta endorphin, norepinephrine and cholinesterase which are highly correlated with the pain/pleasure centers of the central nervous system.

In operation, the present invention involves two functional attributes. The first involves the generation of the complex waveform of a select signature. The second attribute is directed to the implementation of the treatment in a delineated treatment regimen.

With the above overview in mind, attention is first directed to FIG. 1 which presents the various components of the complex waveform of the present invention. More particularly, and starting with FIG. 1A, a graphical representation is provided of the carrier frequency for one specific time segment. In this representation, the carrier frequency equals 15 kilohertz. The amplitude is 40.0 volts peak max (DC) with a duty cycle of 50%. The waveform contains 25 bursts of 15 pulses for each burst. The period for each burst is 2 milliseconds and the period for each pulse is 66.7 microseconds. For each, the burst and the pulse, the duty cycle is 50% on time. Continuing, FIG. 1B presents the first modulation to the carrier frequency. In this example, the first modulation has a frequency of 15 Hertz and a duty cycle of 75%. The second modulation is depicted in FIG. 1C. The second modulation has a frequency of 500 Hertz and a 50% duty cycle. Continuing through FIG. 1D, the complex waveform combining the components depicted in FIGS. 1A through 1C are presented.

The complex waveforms of the present invention may be generated with sinusoidal, sawtooth, hyperbolic or other wave shapes; for simplicity and clarity, the waveforms presented in FIGS. 1A through 1E and further discussed below have been exemplified by simple square waves.

A cycle for the waveform will consist of 50 milliseconds "on" time, in which the pulses for that frequency combination are generated, and an "off" time of 16.7 milliseconds.

Figure 1B:
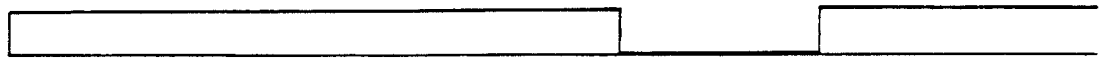
Figure 1C:
Figure 1D:
Figure 1E:
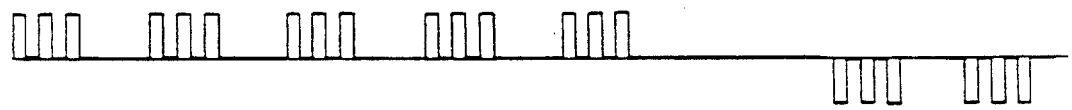

Finally, in FIG. 1E, a complex waveform according to the present invention is provided, in which the polarity of the output is switched from positive to negative on a periodic basis, e.g., 67 milliseconds. This is contrasted with the waveform of FIG. 1D in which the polarity remains positive throughout the cycle; the pulsed DC waveform of FIG. 1D is considered a monopolar output while the output depicted in FIG. 1E is considered bipolar.

For purposes of rough approximation, the energy dissipation in using the present invention is represented by the area under the pulses depicted in FIG. 1D. It can, therefore, be recognized that by adding the second modulation, having a 50% duty cycle, results in a 50% decrease in power dissipation.

The circuit is presently provided with one of the following frequency combinations, but is not limited to:
1) 15 Hz, 500 Hz, 15,000 Hz—Monopolar;
2) 15 Hz, 500 Hz, 15,000 Hz—Bipolar (7.5 Hz);
3) 15 Hz, 500 Hz, 60,000 Hz—Monopolar; or
4) 15 Hz, 4,000 Hz, 60,000 Hz—Monopolar.

As noted above, the invention provides an optional third modulation of the carrier wave having a frequency range of 0.1 Hz to 1,000 Hz, more preferably 1–50 Hz, and most preferably 5–25 Hz. In this embodiment, preferred complex waveforms are derived from the following components: a carrier frequency of 1 KHz to 300 GHz, preferably 100 MHz to 200 GHz, more preferably 20–100 GHz, and most preferably 50–75 GHz; a first modulation frequency of 10–1000 Hz, most preferably 500±50 Hz; a second modulation frequency of about 15 KHz±5 KHz, more preferably ±3 KHz, and most preferably ±2 KHz; and a third modulation frequency in the range of 1–50 Hz, most preferably 15±5 Hz. The present invention can thus be generally described as generating an n-modulated complex waveform.

Figure 2:
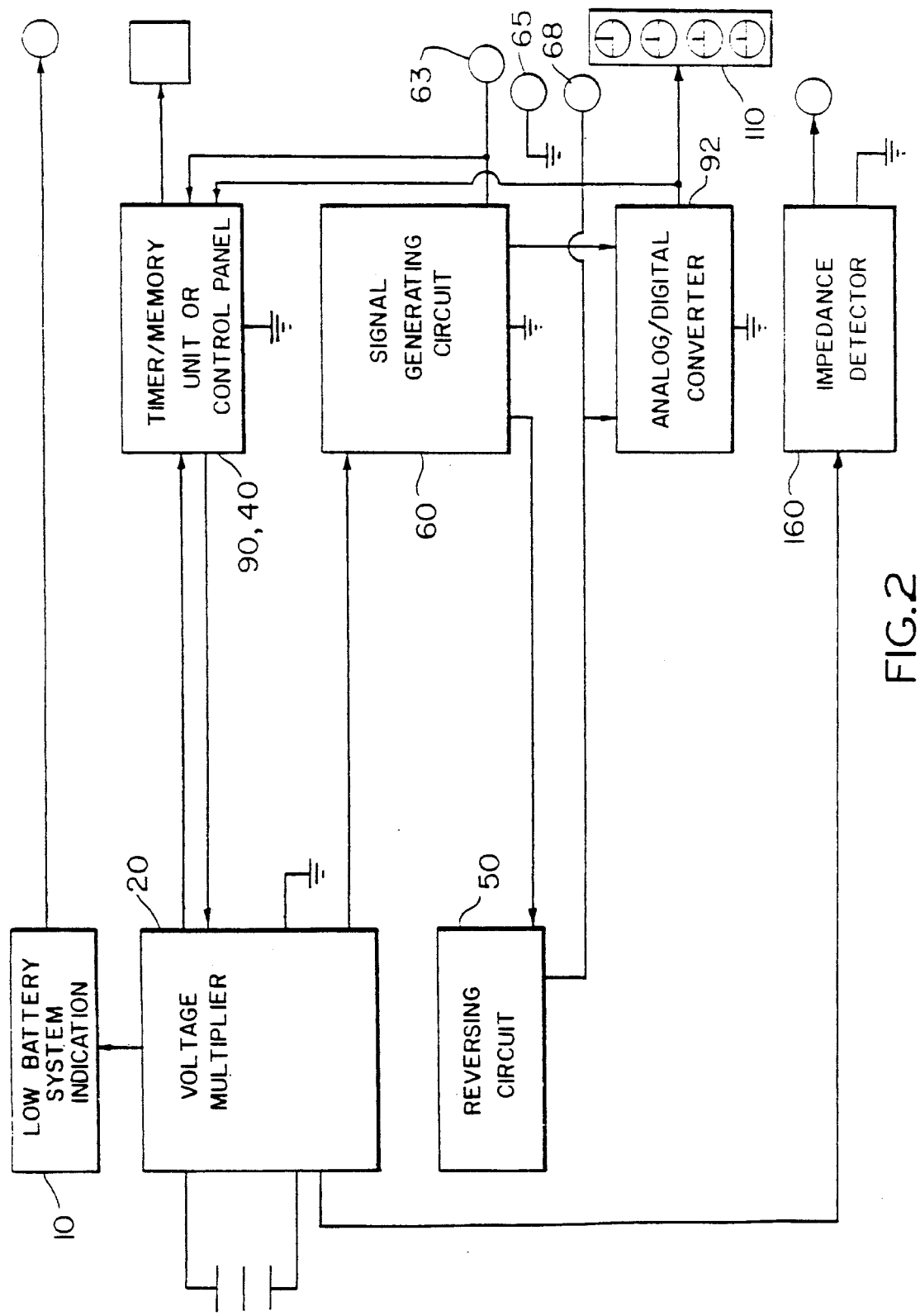
FIG. 2 is a block diagram of the inventive apparatus for generating the waveform depicted in FIG. 1.

Turning now to FIG. 2, the functional elements of the inventive device are presented. The power source to the present system will either be a battery having nominal 9 volt terminal voltage or some rectified and properly transformed line (AC) power source. The battery provides the basic DC power source for generating the complex waveform. This is channeled and controlled by the voltage multiplier, 20. The output of the voltage multiplier 20 which is between 27 v to 40 v, is fed to signal generating circuit 60 which is the oscillating circuit that converts the constant DC output into the complex waveform having the desired characteristics.

The specific constant current and current limited waveform generated by signal generating circuit 60 is pre-set by entering the various frequency settings for the two modulations, and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from memory 40.

The signal generating circuit 60 receives the voltage of 27 v to 40 v from the voltage multiplier. Within the signal generating circuit 60, the voltage branches off into a carrier frequency and two modulation frequencies. An example of the branching of the waveform is depicted in FIGS. 1A–1C.

In FIG. 2, the system supports two separate probes for placement on the patient. Probe 63 represents the positive terminal as generated by signal generating 60. The second probe 65, is grounded within the circuit. For operation applying a bipolar waveform, the probes are connected to terminals 65 and 68, respectively. Terminal 68 is the output from reversing circuit 50, which may be present and which acts to flip the signal generating circuit pursuant to pre-set timing constraints.

The following ancillary systems are also present in this circuit. The low battery and system on indicator 10 which monitors the battery output via voltage multiplier 20 generates an alarm signal when battery output voltage drops below the preset limit, say 7.0 volts. It also shuts the system down if the battery voltage falls below the preset limit of approximately 6.0 volts.

The analog/digital converter 92 converts the signal from the signal generating circuit 60 so that the patient can read it. The analog/digital converter 92 reads the level of output and converts it to the appropriate signal for the four gate integrated circuit which uses that signal to turn on the appropriate sequence of four LEDs 110.

Finally the impedance detector 160 is used to determine if the system is being used on a person (as opposed to someone just running the system without attaching it to a person).

Figure 3:
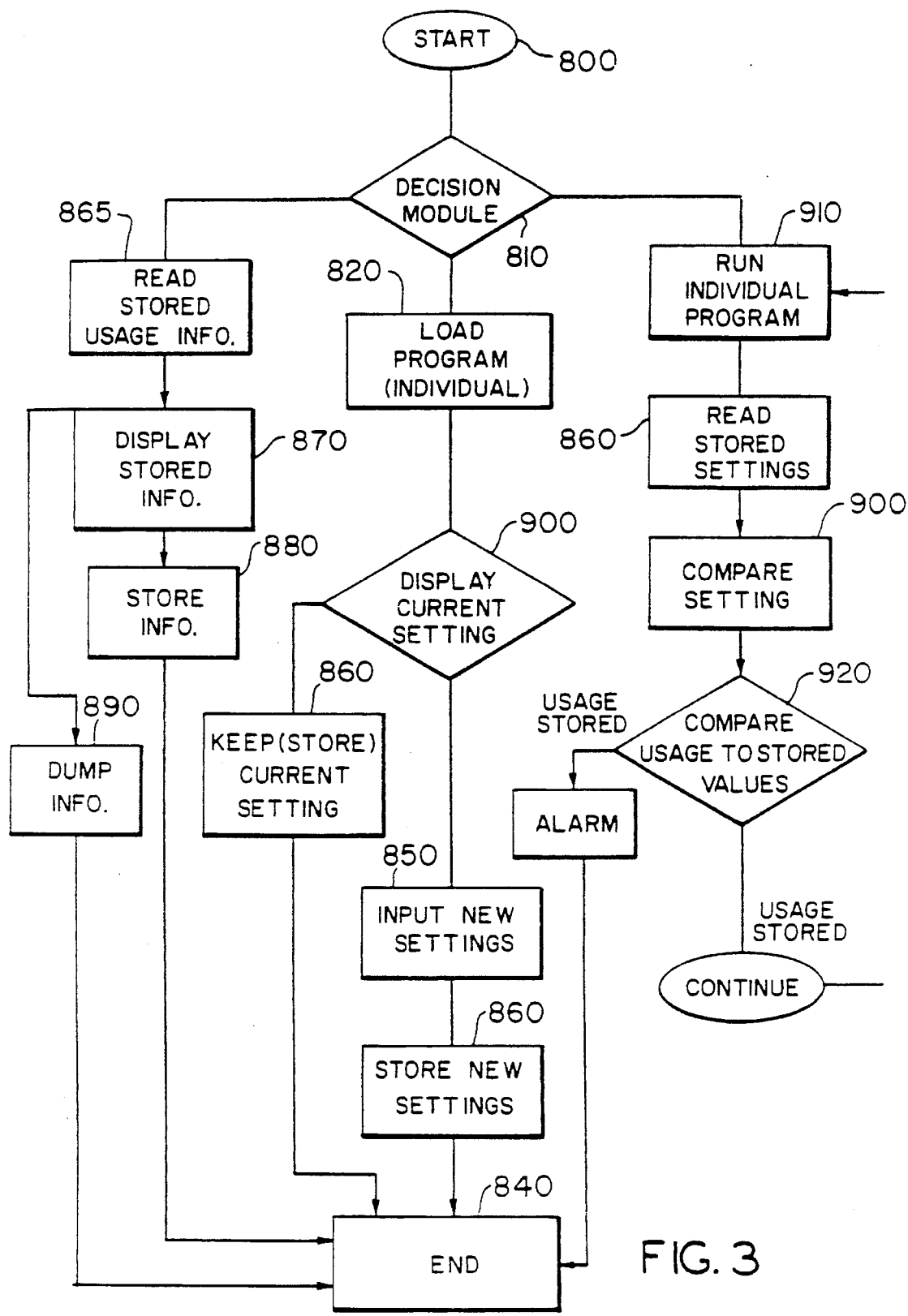
FIG. 3 is a logic flow chart of the data processing program controlling the operation of the apparatus of FIG. 2.

FIG. 3 depicts an exemplary flow chart of the timer unit 90 which the apparatus will use to monitor usage by the patient. A computer program embodying the protocol shown in the flow chart operating in combination with the present invention will prevent the patient from misusing the apparatus, and will allow the physician to set an individual treatment program and to monitor the patient's compliance to the set program.

The timer unit 90 will allow the therapist to set the number of days the system is to be used, the number of times per day the system will be used, and the time duration for each use.

The program will start 800 with an Origination Decision module 810. The Origination Decision Module 810 will give the therapist three choices for use. If the Individualized Program 820 pathway is chosen, the timer unit will load the Individualized Program 820. Then the Individualized Program will begin with a display showing the Current Setting 900, for each of the parameters (i.e. the number of days of use, the number of times per day of use and the length of time for each use). Next the program will ask the therapist whether he wants to Keep the Current Settings 900, or Input New Settings 830. If the therapist wishes to use the same settings as are already registered in the program, the Individualized Program 820, will Store 860 the values and will End 840. However, if the therapist wishes to change the settings, the program will proceed to the Change Input Values 850 module in which the computer will ask the therapist for the new values for the settings. Then the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870, and the therapist will decide whether to store the patient information in the Patient Storage Module 880, or else it will Dump the information 890 and it will End 840.

A final selection which the therapist may access through the Origination Decision Module 910, is actually to use the system. If this choice is the inputted selection, the Run Timed Program 910 will be initialized. The Run Timed Program 890 will read the stored 860 values. Then the program will Check 920 the Stored 860 values against the Current Running Settings 900 which is the values of the Run Timed Program 890 for this usage of the system. If the Current Running Settings 900 for the number of days of use is greater than the Stored 860 values, the program will End 840 without the system being turned on. Next, the Run Timed Program 890 will check the value of the Stored 890 values for the number of uses for a given day and if the Current Running Settings 900 is greater than the Stored 890 values for number of uses for a day, the system will End 840 for that day and the system will not be able to be used until the next day. Finally, as the system is being used, a Running Time Clock will be compared to the Run Timed Program, 890, and when the Current Running Settings in 900 is greater than the Stored 890 values for the length of time for that session, the system will End 840 for that session and the system will not be able to be used until the next session period.

The chart depicted in FIG. 4 demonstrates the effects on the ACTH, cortisol, beta endorphin and serotonin, biochemical neurotransmitter concentrations of patients having been treated with the inventive apparatus having two modulation frequencies. Multiple tests were made on three normals and other normal volunteers using monopolar, bipolar, and placebo instruments on a double blind basis. The symbol "n" denotes how many samples were made for each type of test. All tests for two of the three normals were made at the same time of day, the third normal was done always at 8 a.m. each morning and the 10 volunteers were processed at 10 a.m. to 12 noon for all their testing.

As is shown in the chart, the results on the tested neurotransmitters were marked. In each, the bipolar application had the greater effect on the neurotransmitter, with the monopolar still having significant results in its own right.

Turning to the improved invention relating to iontophoretic transdermal delivery, the present invention, most preferably with two modulating frequencies, is applicable to the topical delivery of virtually any pharmaceutical agent which has a charge or can be formulated in a carrier such that the molecule has a charge or a dipole. As is commonly known in techniques which use electrokinetic phenomena, such as electrophoresis and electroosmosis, a charged species will tend to migrate in a medium depending on the relationship of the average charge (i.e., positive or negative) on the species to the charge applied to the liquid medium in which the species is present in solution. For example, when it is desirable to use a certain drug having a negative charge, the drug in an appropriate carrier is applied topically to the area to be treated and the negative electrode (of the foregoing apparatus) is applied in contact with the same patient area. Because the negatively charged drug will be repelled by the negative electrode, the drug will migrate away from the electrode, and thus transdermally into the patient's tissues.

It is important to note that the present invention, when used for iontophoretic delivery, provides a waveform which is preferably exclusively monopolar. This arrangement is in contrast to the teachings of the prior art, such as Sibalis, which teach the use of alternating current. We have found that the use of a monopolar waveform, such as that shown in FIG. 1D, provides improved transdermal deliver by virtue of the avoidance of a reversal in polarity which will tend to reverse or slow the transdermal delivery of the drug. Additionally, the use of a monopolar complex waveform allows for reduced electrical energy to be applied to the patient to achieve a particular dosage; especially since additional energy is not required to compensate for the application of an alternating current waveform which impedes the transdermal delivery. While not preferred, it may be desirable in some situations to provide a waveform that is essentially monopolar, that is, a bipolar waveform in which one polarity dominates (is present for a longer period of time) the reverse polarity; of course, the dominant polarity is that which is effective in delivering the pharmaceutical agent to the patient.

The present invention is applicable to the delivery of a wide variety of pharmaceutically active agents, including anti-inflammatory agents like hydrocortisone, proteins and/or hormones such as insulin, nicotine, antianginal and/or vasodilator compounds such as nitroglycerin, vitamins and cofactors such as nicotinic acid, antihypertensives such as propranolol, and anesthetics such as lidocaine, some of which are commonly used in transdermal patches and other topically-applied compositions. By the term "topical" is meant the direct iontophoretic administration of the pharmaceutical agent, whether on the surface of the skin (dermis), eye, gum, or anywhere on the body on which electrodes can be conveniently located.

The present invention also has significant use in the iontophoretic delivery of psychoactive and neuroactive agents. As described previously and shown in FIG. 4, the neuroaugmentive apparatus of this invention can increase the levels of serotonin, beta-endorphin, GABA, and other neural transmitters and controlling molecules. Accordingly, the administration of an analgesic, if not a psychoactive or neuroactive agent, can be further enhanced by the synergistic increase in such neurotransmitters.

When the apparatus is used for iontophoretic delivery, a monopolar signal is more preferred. The carrier frequency (e.g., as shown in FIG. 1A) ranges from about 1 Hz to about 300 KHz, and facilitates the penetration of the total electrical signal; more preferably the carrier signal ranges from about 10 Hz to about 100 KHz, and most preferably ranges from 10–50 KHz. The first modulating signal is the "bio-active" frequency which, without desirous of being constrained to any particular theory, is believed to enhance the neurobiochemical levels in both the cerebral spinal fluid and in the blood plasma, such as by altering the permeability of synapses and other cellular membranes to various ions. This first modulating signal ranges from about 10 Hz to about 199 KHz, more preferably from about 10 Hz to about 50 KHz, and most preferably is in the range of 10–100 Hz. The second modulating signal is analogous to a "tuning" frequency and can be used to reduce the aggregate energy delivered to the patient during the "on" portion of the duty cycle. The second modulator ranges from 100 Hz to 300 KHz, more preferably from 100 Hz to 100 KHz, and most preferably in the range of 100–1,000 Hz. A preferred embodiment of the iontophoretic delivery device uses a carrier signal of about 15 Khz, a first modulator of about 10 Hz, and a second modulator of about 500 Hz.

The particular drug or combination of drugs to be administered is provided in a suitable carrier by methods well-known to the artisan. It is preferable to formulate a solution, gel, or mixture of the drug for delivery through moist electrodes which are commonly used and available, and analogous to those described by Sibalis. It is also preferable to use a chemical penetration enhancer, such as DMSO (dimethyl sulfoxide), to assist in diffusion of the pharmaceutical agent into the patient's tissues.

The embodiment of the above description has been based on discrete components to enhance the understanding of the functional characteristics of the system. Numerous modifications and adaptations thereof will be readily apparent to those skilled in the art without departing from the spirit and scope of the present invention.

What is claimed is:

1. In combination, in a system for the iontophoretic topical delivery of a pharmaceutically active agent, said system comprising:
   a. means for generating a substantially constant current pulsed DC output voltage;
   b. means for converting said output voltage into an n-modulated output adjustable constant current waveform, wherein n is an integer;
   c. a pharmaceutically active agent effective for topical administration;
   d. contact means for containing and delivering said pharmaceutically active agent to a topical area of a patient in need of treatment, said contact means including at least two electrodes;
   e. means for directing said n-modulated output waveform to said contact means;
   wherein said n-modulated output waveform comprises a first waveform component ranging between 1 and 300,000 KHz, a second waveform component ranging between 10 and 199,000 Hz, and a third waveform component ranging between 100 and 300,000 Hz, and each waveform component is substantially time invariant and distinct from said other waveform components, said double modulated output waveform having a monopolar characteristic.

2. The system of claim 1 wherein said first waveform component has a 50% duty cycle, and said second waveform component has a 75% duty cycle but not limited thereto.

3. The system of claim 1, wherein the first waveform ranges from about 10 Hz to about 100 KHz.

4. The system of claim 3, wherein the first waveform ranges from about 10–50 KHz.

5. The system of claim 4, wherein said second waveform component ranges from about 10 KHz to about 20 KHz.

6. The system of claim 1, wherein said third waveform ranges from about 100 Hz to about 100 KHz.

7. The system of claim 1, wherein said first waveform component is approximately 15,000 Hz, said second waveform component is approximately 15 Hz, and said third waveform component is approximately 500 Hz.

8. The system of claim 1, wherein the pharmaceutical agent is selected from the group consisting of anti-inflammatory agents, proteins and/or hormones, nicotine, antianginal and/or vasodilator compounds, vitamins and cofactors, antihypertensives, and anesthetics.

9. The system of claim 8, wherein the pharmaceutical agent is selected from the group consisting of hydrocortisone, insulin, nicotine, nitroglycerin, nicotinic acid, propranolol, and lidocaine.

10. In combination, in a system for the treatment of certain neural responsive conditions, said system comprising:
    a. means for generating a substantially constant current pulsed DC output voltage;
    b. means for converting said output voltage into an n-modulated output adjustable constant current waveform;
    c. contact means comprising at least two contacts for conducting said n-modulated output adjustable constant current to a mammalian host:
    d. means for directing said n-modulated output waveform across said at least two contacts;
    wherein said n-modulated output waveform comprises a first waveform component ranging between 1 KHz and 300 GHz, a second waveform component ranging between 1 and 199,000 Hz, a third waveform component ranging between 100 and 300,000 Hz, and a fourth waveform component ranging from 0.1 Hz to 1,000 Hz, each waveform component being substantially time invariant and distinct from said other waveform components, said n-modulated output waveform having a monopolar characteristic.

11. The system of claim 10, wherein said first waveform component has a 50% duty cycle and said second waveform component has from about a 50% duty cycle to about a 75% duty cycle.

12. The system of claim 10, further comprising a means for intermittently reversing polarity of said n-modulated waveform.

13. The system of claim 10, wherein said first waveform component is a carrier frequency of 20–100 GHz.

14. The system of claim 10, wherein said second waveform component is a modulation frequency in the range of 10–1000 Hz.

15. The system of claim 10, wherein said third waveform component is a modulation frequency of 15 KHz±5 KHz.

16. The system of claim 10, wherein said fourth waveform component is a modulation frequency in the range of 1–50 Hz.

17. The system of claim 10, wherein said first waveform component has a frequency in the range of 50–75 GHz, said second waveform component has a frequency in the range of 500±50 Hz, said third waveform component has a frequency in the range of 15 KHz±2 KHz, and said fourth waveform has a frequency in the range of 5–25 Hz.

18. In combination in a method for the treatment of pain or symptoms of neural dysfunction distress, comprising the steps of:

a. developing a treatment regimen comprising a series of individual treatment sessions;

b. programming an n-modulated waveform generator with said treatment regimen;

c. monitoring and recording an implementation of said treatment regimen with said n-modulated waveform generator; and d. replaying a historical account of said treatment regimen for review;

wherein said n-modulated waveform generator generates a first waveform component ranging between 1 KHz and 300 GHz, a second waveform component ranging between 10 and 199,000 Hz, a third waveform component ranging between 100 and 300,000 Hz, and fourth waveform component ranging from 0.1 Hz to 1,000 Hz.

19. The method of claim 18, wherein said first waveform component has a frequency in the range of 50–75 GHz, said second waveform component has a frequency in the range of 500±50 Hz, said third waveform component has a frequency in the range of 15 KHz±2 KHz, and said fourth waveform has a frequency in the range of 5–25 Hz.

20. The method of claim 18, wherein said waveform generator further includes an abuse-preventing circuit that automatically stops any waveform output when usage exceeds a pre-programmed limit.

* * * * *